(12) United States Patent
Sajó et al.

(10) Patent No.: US 7,391,041 B2
(45) Date of Patent: Jun. 24, 2008

(54) GERMICIDAL UV REACTOR AND UV LAMP

(75) Inventors: Gábor Sajó, Julianus barát (HU);
Katalin Tóth, Viola (HU)

(73) Assignee: General Electric Company, Schenectady, NY (US)

(*) Notice: Subject to any disclaimer, the term of this patent is extended or adjusted under 35 U.S.C. 154(b) by 392 days.

(21) Appl. No.: 11/255,539

(22) Filed: Oct. 21, 2005

(65) Prior Publication Data

US 2007/0114465 A1 May 24, 2007

(51) Int. Cl.
*G01J 3/10* (2006.01)

(52) U.S. Cl. .............................. 250/504 R; 250/432 R; 250/436; 210/748; 210/764; 210/138; 315/94; 315/101; 422/24

(58) Field of Classification Search ................. None
See application file for complete search history.

(56) References Cited

U.S. PATENT DOCUMENTS 6,707,246 B1 3/2004 Van Den Bogert et al.
2004/0232846 A1 11/2004 Fischer et al.

*Primary Examiner*—Jack I. Berman
*Assistant Examiner*—Zia Hashmi
(74) *Attorney, Agent, or Firm*—Fay Sharpe LLP

(57) ABSTRACT

A germicidal UV reactor for use in fluid purifiers is provided, in which the UV reactor comprises an UV lamp with an UV transparent primary envelope and also an UV transparent secondary envelope around the primary envelope. The outer surface of the secondary envelope is in contact with a flowing fluid to be purified. There is an isolating space between the outer surface of the primary envelope and the inner surface of the secondary envelope. At least one of the outer surface of the primary envelope and the inner surface of the secondary envelope is provided with electrical means for heating and thus enhancing UV emitting efficiency of the UV lamp.

18 Claims, 3 Drawing Sheets

GERMICIDAL UV REACTOR AND UV LAMP

BACKGROUND OF THE INVENTION

This invention relates to a germicidal UV reactor for use in fluid purifiers and to an UV lamp for use in such a germicidal UV reactor.

In the commonly used fluid purifiers, there are germicidal UV reactors used to effect sterilization, disinfection. The possible variety of fluids is wide, covering water, tap water, wastewater, any other water based liquid mixtures, liquid foods and beverages, and also non-water based liquids such as, for example, edible oils. This fluid can also be gaseous, such as air, for example, in case of air conditioners.

The germicidal effect of the UV radiation is well known. Published U.S. patent application Ser. No. 2004/0232846 discloses an amalgam mercury low pressure UV lamp. In order to reach an optimum temperature during operation of the lamp, means are provided for influencing the temperature of the amalgam. Common UV lamps used in germicidal UV reactors are not immersed directly into the liquid to be treated and disinfected. The temperature of the flowing water or other liquid is usually too low to maintain the necessary operating temperature of the UV lamp. Therefore, the lamp is sheathed in an UV transparent cladding tube, which results in an air gap between its inner wall and the outer envelope of the UV lamp. The low thermal conductivity of air guarantees at steady operation of the UV lamp that the latter will not cool down below the optimum temperature range. In some cases, however, the air gap is quite narrow in order to provide sufficient UV density at the surface of the cladding tube. The narrow gap diminishes its thermal resistance and thus the cooling effect on the envelope of the UV lamp.

The ignition of the UV lamp requires some time, in the order of a minute, until the desired operational germicidal efficiency is reached. Usually, continuous lamp operation is suggested, e.g. in water disinfection reactors, due to the long warm up period of germicidal UV lamps. In case of non-continuous lamp operation, the UV lamp is switched on only when water starts flowing. The germicidal effect is significantly reduced at non-continuous operation due to the long warming up of standard fluorescent UV lamp. U.S. Pat. No. 6,707,246 discloses a low-pressure mercury vapor discharge lamp with a discharge vessel, which is provided with auxiliary amalgam. This lamp has an improved warm-up characteristic whereby the lamp has a relatively short run-up time during the starting period. However, an immediate effect right after switching on is not yet expectable. Furthermore, the lamp temperature can vary over a longer period, e.g. in use of an UV reactor when the temperature of the flowing fluid changes.

Thus there is a particular need for an UV reactor for use in fluid purifiers and an appropriate UV lamp for the reactor in which the maximum germicidal efficiency is steadily provided both in quasi-immediate manner after switching on and during a long time use under changing external thermal conditions.

BRIEF SUMMARY OF THE INVENTION

In an exemplary embodiment of the invention, a germicidal UV reactor for use in fluid purifier is provided. The UV reactor comprises an UV lamp having an UV transparent primary envelope with an outer surface, an UV transparent secondary envelope around the primary envelope and having an outer surface being in contact with a flowing fluid to be purified and an inner surface facing the UV lamp. There is an isolating space between the outer surface of the primary envelope and the inner surface of the secondary envelope. At least one of the outer surface of the primary envelope and the inner surface of the secondary envelope is provided with electrical means for heating.

In an exemplary embodiment of another aspect of the invention, an UV lamp for use in germicidal UV reactor of a fluid purifier is provided. The lamp comprises an UV transparent envelope. The outer surface of the envelope is provided with electrical means for heating.

This arrangement provides optimum thermal conditions for the UV lamp with a negligible loss of UV light due to the additional means for heating.

Such UV lamps and such germicidal UV reactors for use in fluid purifiers allow an instant use as well since the desired effect appears immediately when the purifier is switched on. This almost doubles the useful life of the germicidal UV lamp and reduces the energy consumption of the purifier.

BRIEF DESCRIPTION OF DRAWINGS

The invention will now be described with reference to the enclosed drawings, where.

DETAILED DESCRIPTION OF THE INVENTION

Figure 1:
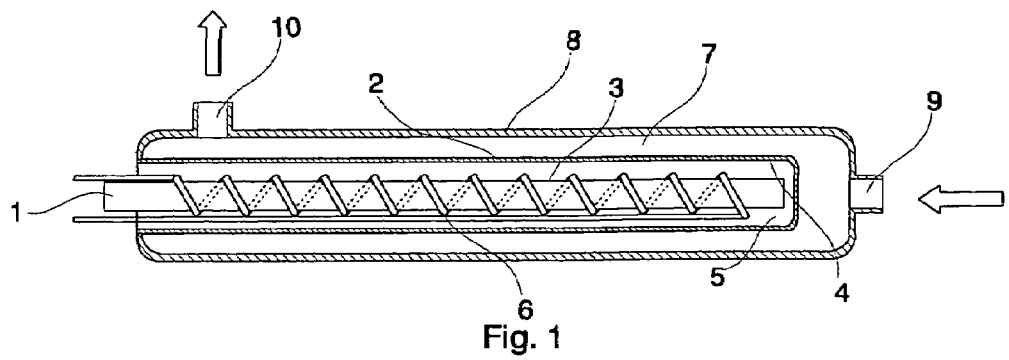
FIG. 1 is a sectional view of a germicidal UV reactor for use in fluid purifiers.

The same functional elements of different embodiments in the drawings are identified by the same reference numbers.

In FIG. 1, a typical UV reactor 8 for use in a fluid purifier is illustrated in its sectional view. The UV reactor 8 has a fluid inlet 9 and a fluid outlet 10, and also has an UV transparent cladding tube in which an UV lamp can be inserted. The UV lamp has an elongated primary envelope 1 of cylindrical shape, thus it can be inserted concentrically into the cladding tube. It is to be noted that other cross-sectional shapes, different from the cylindrical, could also be applicable. On one end, the cladding tube is closed and its other end is mounted inside of the reactor 8 in a fluid tight manner. Thus a fluid space 7 is resulted between the fluid inlet 9 and the fluid outlet 10. The cladding tube separates the inner space including the UV lamp from the fluid space 7, thus this can be regarded in this reactor 8 as a secondary envelope 2 around the primary envelope 1 of the UV lamp. There is an isolating space 5 between the primary envelope 1 and the secondary envelope 2, normally filled with air, other filling gas or vacuum. The outer surface of the secondary envelope 2 is in direct contact with the flowing fluid to be purified, for example water.

Usually, both the primary envelope 1 of the UV lamp and the secondary envelope 2 of the cladding tube are made of quartz glass, providing excellent UV transparency even together.

The outer surface of the primary envelope 1 and the inner surface of the secondary envelope 2 are in thermal coupling with each other through the isolating space 5. The measure of this thermal coupling is depending on the width and the filling gas of the isolating space 5. Typically, the width of the isolating space 5 is small, constituting practically a gap only between the primary and secondary envelopes 1 and 2. The flowing fluid to be purified is often colder than the outer surface of the primary envelope 1 of the UV lamp.

Figure 2:
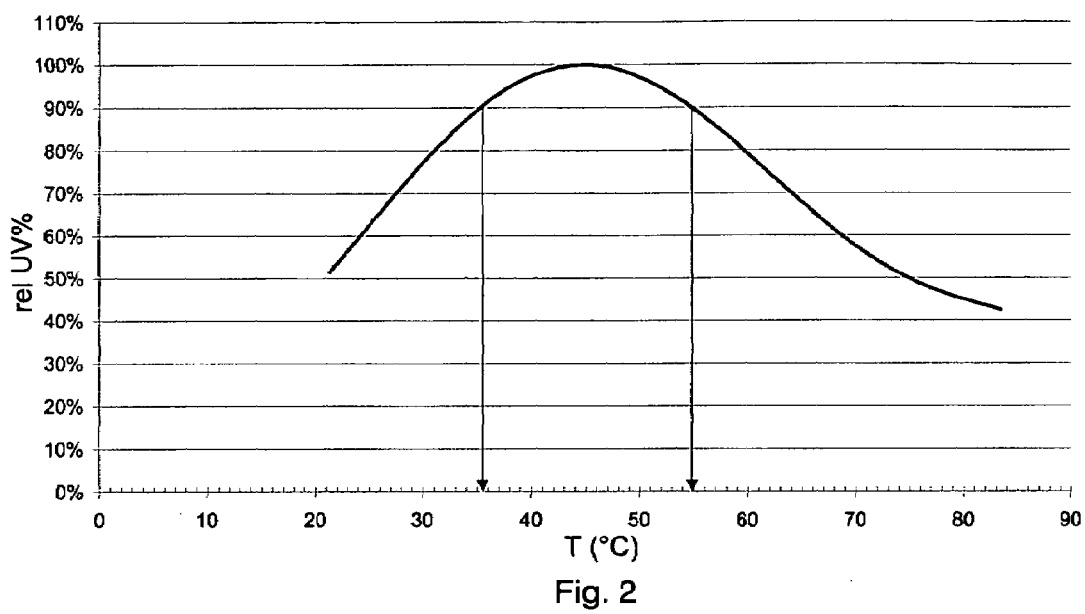
FIG. 2 is a diagram of relative UV emission vs. lamp temperature of an UV lamp.

The UV efficiency of an UV lamp is dependent on its envelope wall temperature. This is illustrated in FIG. 2, where the diagram of relative UV emission vs. lamp temperature of an UV lamp clearly shows that this efficiency is above 90% only within a temperature range. It is known that that the lowest temperature at a so-called "cold spot" defines the mercury gas pressure in a fluorescent lamp, and thus defines the actual UV efficiency of the lamp. Consequently the temperature of the lamp or its cold spot at least is to be maintained within a range. For a fluorescent UV lamp generally used in the practice of purifiers, this range is about 35-55° C., as it can be seen in FIG. 2. However, the most appropriate temperature would be around 45° C.

Figure 3:
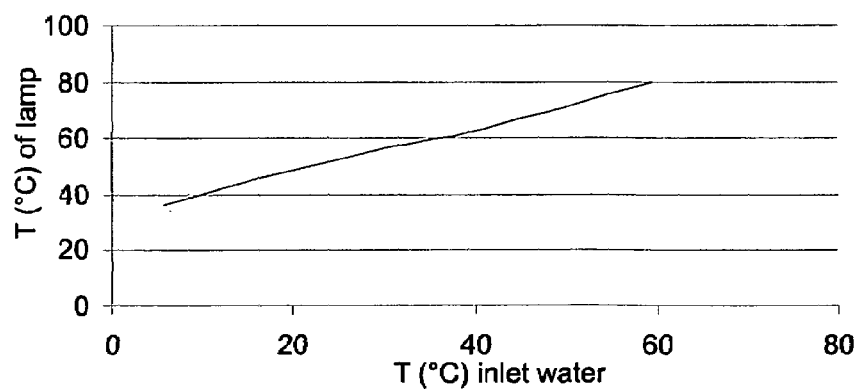
FIG. 3 is a diagram of lamp temperature vs. inlet water temperature in a water purifier.

FIG. 3 is a diagram of an UV lamp temperature, more particularly its primary envelope temperature, vs. inlet water temperature in a water purifier according to FIG. 1, for example. This diagram shows that at least about 25° C. inlet water temperature would provide the optimum operating temperature. In most cases, however, the temperature of the flowing fluid, for example water, has a significantly lower temperature.

In order to provide optimum UV efficiency, an electrical means for heating 6 has been introduced. It was found that this means for heating 6 can be applied either to the outer surface 3 of the primary envelope 1 or to the inner surface 4 of the secondary envelope 2. Furthermore, this means for heating 6 can also be applied to both surfaces 3 and 4 at the same time.

Figure 4:
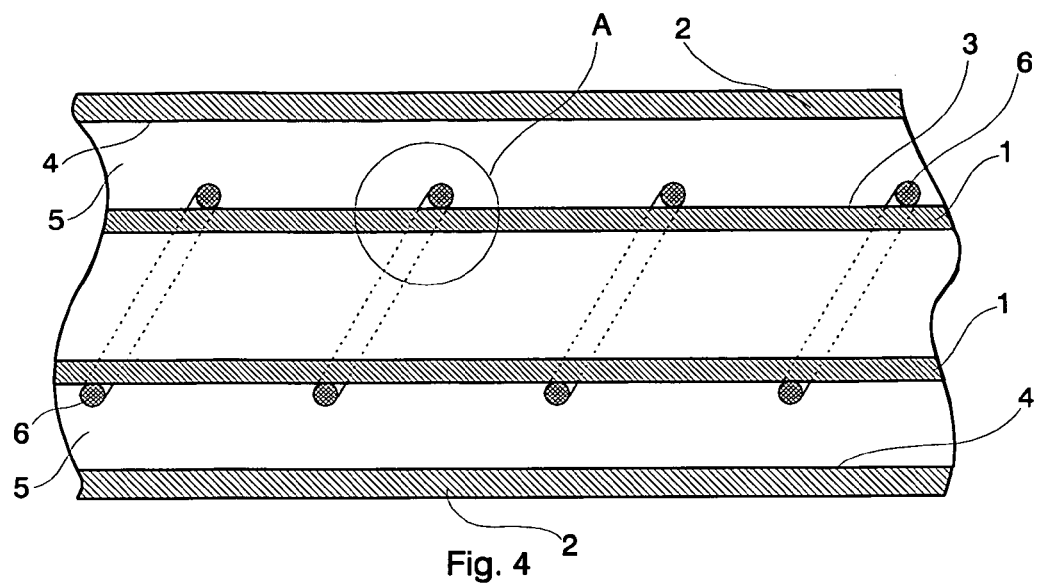
FIG. 4 is a sectional view of an UV reactor including an UV lamp according to an embodiment of the invention.

In an embodiment of FIG. 4, the means for heating 6 is a filament applied on the outer surface 3 of the primary envelope 1 of the UV lamp. In a simple case, a common filament of round cross-section is spooled on the primary envelope 1. While in FIG. 1, this filament is spooled on the primary envelope 1 at its whole length, it can be sufficient to spool the filament onto the primary envelope 1 only in a part of its length. The ends of the filament are coupled to contact means, not indicated in FIG. 4. Through this contact means, the electrical means for heating 6 is powered from an electrical supply. This may be, in an embodiment, separate from the power supply of the UV lamp. This has an advantage that the heating effect may be independent from the main supply of the UV lamp either in time or in power. The electrical means for heating 6 can be powered from a regulated electrical supply controlled by a measurement signal of a thermal detector. The thermal detector may be placed in the isolating space 5. This control may be taken place by any known feedback circuitry.

Figure 5:
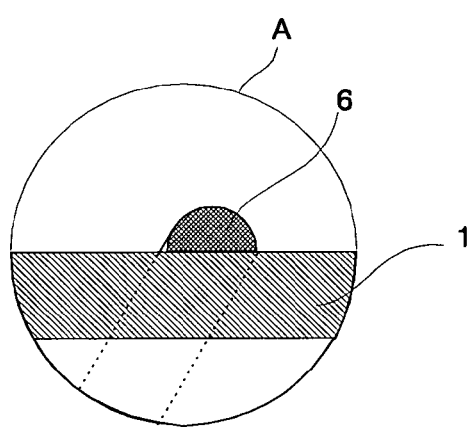
FIG. 5 is an enlarged and modified part A of FIG. 4.

FIG. 5 shows an enlarged and at the same time slightly modified part A of FIG. 4. The modification lies in the cross-section of the used filament, which now is a half circle, the flat part of which provides a better thermal contact with the outer surface 3 of the primary envelope 1.

Figure 6:
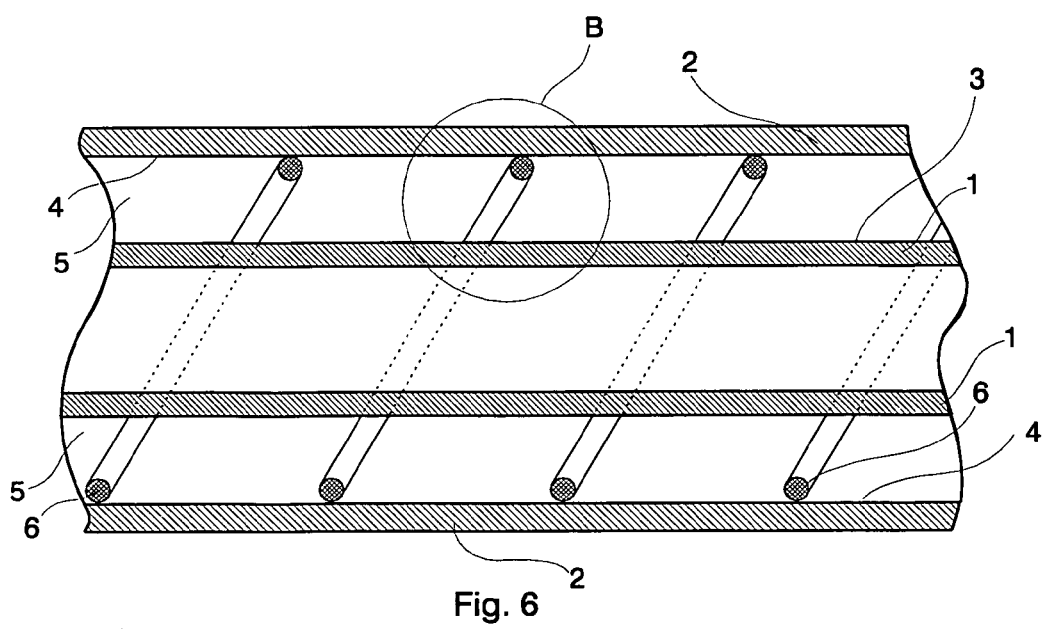
FIG. 6 is a sectional view of an UV reactor including a further embodiment of the invention.

An alternative embodiment is illustrated in FIG. 6. It shows a main part of an UV reactor in sectional view. The difference from the embodiment of FIG. 4 is the location of the applied filament as means for heating 6. The filament here is applied to the inner surface 4 of the secondary envelope 2. In this embodiment, the heating effect is transferred through the isolating space 5, which causes more even temperature distribution over the outer surface 3 of the primary envelope 1.

Figure 7:
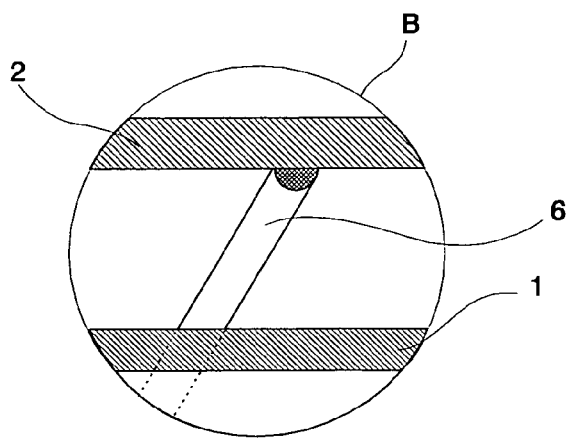
FIG. 7 is an enlarged and modified part B of FIG. 6.

FIG. 7 shows an enlarged part B of FIG. 6. This includes a modification similar to that of part A of FIG. 5. The modification also lies in the cross-section of the used filament, which is a half circle again, the flat part of which provides a better contact with the inner surface 4 of the secondary envelope 2. This may be an advantage when the filament as means for heating 6 is glued to the concave inner surface 4 of the secondary envelope 2.

In further embodiments of the invention, the means for heating 6' is manufactured by coating a patterned electrically conductive layer, similar to that in heated vehicle windows and windscreens. The metallic layer evaporated or deposited by any known technology constitutes a pattern either on the outer surface 3 of the primary envelope 1 or on the inner surface 4 of the secondary envelope 2.

Figure 8:
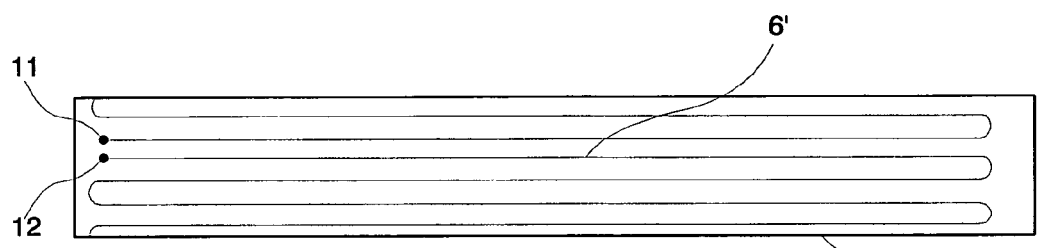
FIG. 8 is a side view of a further embodiment of the UV lamp of the invention.

FIG. 8 shows a meander of metal coating on the primary envelope 1 in a simplified view. Contact means 11 and 12 render it possible to connect the means for heating 6' to a power supply.

Figure 9:
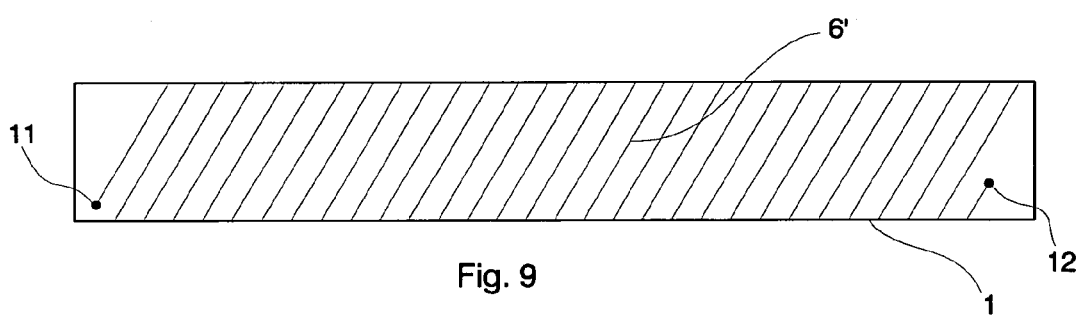
FIG. 9 is a side view of an even further embodiment of the UV lamp of the invention.

FIG. 9 shows a spiral metal coating on the primary envelope 1 in a simplified view. Contact means 11 and 12 are provided also to connect the means for heating 6' to a power supply, but in this embodiment on opposite ends of the primary envelope 1.

Figure 10:
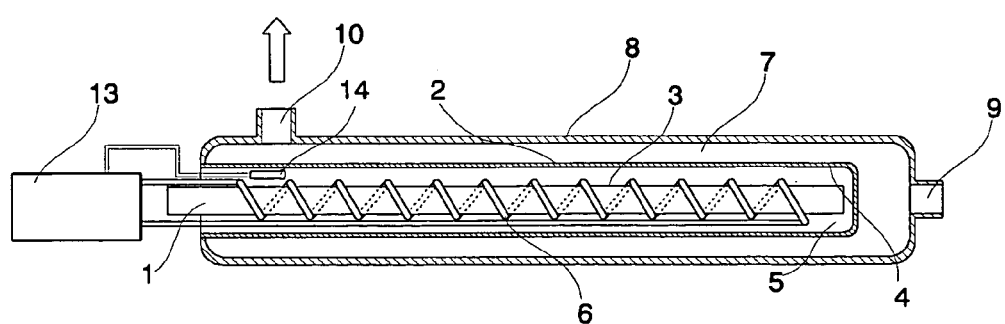
FIG. 10 is a germicidal UV reactor with a regulated electric supply.

It is illustrated in FIG. 10 that the electrical means for heating 6 can be powered from a regulated electrical supply 13 controlled by a measurement signal of a thermal detector 14. This thermal detector 14 can be placed in the isolating space 5. The electrical supply 13 is separate from the power supply of the UV lamp. The other elements of FIG. 10 are corresponding to those of FIG. 1.

The above described means for heating covers a certain fraction of the surface of the primary and/or secondary envelopes, which may obstruct UV light emission. This is, however, such a little fraction that the enhanced UV emitting efficiency yields much more additional UV light than the loss due to the shielding of the filaments or coatings.

The foregoing have been illustrative, but non-limiting examples of the practice of the invention. As will be appreciated by those skilled in the art, other embodiments of the means for heating may be applied to the UV reactors or the UV lamps, including multi-layer coatings or embedded filaments. Those skilled in the art will also appreciate that the invention is applicable to any kind of sterilization of flowing liquid or gaseous fluids by UV lamps.

The invention claimed is:

1. A germicidal UV reactor for use in fluid purifier, the UV reactor comprising
    an UV lamp having an UV transparent primary envelope with an outer surface;
    an UV transparent secondary envelope around the primary envelope and having an outer surface being in contact with a flowing fluid to be purified and an inner surface facing the UV lamp;
    an isolating space between the outer surface of the primary envelope and the inner surface of the secondary envelope;
    at least one of the outer surface of the primary envelope and the inner surface of the secondary envelope being provided with electrical means for heating.

2. The UV reactor of claim 1, in which the electrical means for heating is a filament.

3. The UV reactor of claim 2, in which the filament, at least in a part of its length, is spooled on the outer surface of the primary envelope.

4. The UV reactor of claim 2, in which the filament is adapted to the inner surface of the secondary envelope.

5. The UV reactor of claim 3, in which the cross-section of the filament is a half circle, the flat part of which is in contact with the outer surface of the primary envelope.

6. The UV reactor of claim 4, in which the cross-section of the filament is a half circle, the flat part of which is in contact with the inner surface of the secondary envelope.

7. The UV reactor of claim 1, in which the electrical means for heating is a pattern of electrically conductive surface coating.

8. The UV reactor of claim 7, in which the pattern of electrically conductive surface coating is applied to the outer surface of the primary envelope.

9. The UV reactor of claim 7, in which the pattern of electrically conductive surface coating is applied to the inner surface of the secondary envelope.

10. The UV reactor of claim 1, in which the electrical means for heating is powered from an electrical supply separate from the power supply of the UV lamp.

11. The UV reactor of claim 1, in which the electrical means for heating is powered from a regulated electrical supply controlled by a measurement signal of a thermal detector.

12. The UV reactor of claim 11, in which the thermal detector is placed in the isolating space.

13. An UV lamp for use in germicidal UV reactor of a fluid purifier, the lamp comprising an UV transparent envelope having an outer surface;

the outer surface of the envelope being provided with electrical means for heating.

14. The UV lamp of claim 13, in which the electrical means for heating is a filament.

15. The UV lamp of claim 13, in which the filament, at least in a part of its length, is spooled on the outer surface of the envelope.

16. The UV lamp of claim 13, in which the electrical means for heating is a pattern of electrically conductive surface coating.

17. The UV lamp of claim 13, in which the electrical means for heating is powered from an electrical supply separate from the power supply of the UV lamp.

18. The UV lamp of claim 13, in which the electrical means for heating is powered from a regulated electrical supply controlled by a measurement signal of a thermal detector.

* * * * *